United States Patent [19]

McMillian

[11] Patent Number: 5,505,712
[45] Date of Patent: Apr. 9, 1996

[54] MEDICAMENT APPLICATOR WITH SPATULATE TIP

[76] Inventor: Ray M. McMillian, 12060 Springdale Lake Dr., Cincinnati, Ohio 45246

[21] Appl. No.: 226,979

[22] Filed: Apr. 13, 1994

[51] Int. Cl.⁶ .................................................. A61M 5/178
[52] U.S. Cl. .................... 604/212; 604/217; 604/289; 604/293; 222/192; 222/420
[58] Field of Search ........................ 604/212, 217, 604/293, 295; 222/420, 206, 192

[56] References Cited

U.S. PATENT DOCUMENTS

| | | | |
|---|---|---|---|
| D. 185,414 | 6/1959 | Dailey | 604/295 X |
| D. 306,831 | 3/1990 | Chevassus . | |
| D. 317,203 | 5/1991 | Walsh . | |
| 411,792 | 10/1889 | Eggers | 604/295 X |
| 821,389 | 5/1906 | Wells | 604/217 |
| 1,678,562 | 7/1928 | Eders | 604/217 X |
| 1,706,249 | 3/1929 | Naun | 604/295 X |
| 2,005,091 | 6/1935 | Kuenstler . | |
| 2,115,959 | 5/1938 | Lewis | 222/420 X |
| 2,330,149 | 9/1943 | Schaaff | 222/420 X |
| 2,520,605 | 8/1950 | Mayrier | 604/217 X |
| 2,854,003 | 9/1958 | Kirsch . | |
| 3,379,196 | 4/1968 | Mitchell . | |
| 4,605,398 | 8/1986 | Herrick | 604/295 X |
| 5,154,702 | 10/1992 | Foyil . | |

FOREIGN PATENT DOCUMENTS

| | | | |
|---|---|---|---|
| 395263 | 7/1933 | United Kingdom | 604/295 |
| 814161 | 5/1959 | United Kingdom . | |

*Primary Examiner*—Mary Beth Jones
*Attorney, Agent, or Firm*—Richard C. Litman

[57] ABSTRACT

A fluid applicator includes a suction bulb, a screw cap, a finger support, an inner shaft, and an outer shaft that ends in a spatulate dispenser. The suction bulb connects with the thin tubular inner shaft, which extends throughout the applicator to terminate at a release opening in the spatulate dispenser. The suction bulb, which is preferably made of rubber or flexible plastic, has a toroidal lower lip that hooks over a complementary toroidal projection of the screw cap. The tubular inner shaft has an upper lip that projects horizontally into contact with the inside of the suction bulb and that rests on the toroidal projection of the screw cap. The screw cap, which is innerly threaded, is positioned immediately above and integral with the oblong winged member that provides finger support for a user. Also integral with the screw cap and finger supports is the outer shaft, which shields the inner tubular shaft and is configured mainly as a cylinder. The spatulate dispenser at the end of the outer shaft has rounded edges, and may be tapered. Within the spatulate dispenser the inner shaft may be strictly tubular or tapered, with a small and mainly circular release opening, or may expand into a broader reservoir having a more extensive release opening. In an alternative embodiment, the inner shaft is eliminated and the outer shaft serves as the receiving tube for the fluid to be applied.

13 Claims, 2 Drawing Sheets

MEDICAMENT APPLICATOR WITH SPATULATE TIP

BACKGROUND OF THE INVENTION

1. Field of the Invention

The present invention relates to a fluid applicator, in particular for use in applying medicine beneath a toenail or fingernail.

2. Description of the Prior Art

Droppers are used extensively for applying fluids, such as medicine, to various areas of the body. Some areas are of course harder to reach than others, and prime among the difficult areas are the portions of flesh under nails. Efficiently transmitting medicine into the nail bed is essential in some situations, such as when combatting fungi, an affliction that can loosen a nail. A poor transmittal of anti-fungal medicine may render the best of such medicines ineffectual, possibly resulting in the loss of the nail concerned. Thus, it is highly desirable to have a fluid applicator that facilitates medicine being applied beneath a toe or finger nail.

Numerous patents have issued related to fluid applicator droppers and related devices. For instance, U.S. Pat. Des. No. 306,831, issued to Alain Chevassus on Mar. 27, 1990, illustrates a dropper that has a broad cylindrical handle area and a thin cylindrical dispensing nozzle that connects to a conical portion. U.S. Pat. Des. No. 317,203, issued to William Walsh on May 28, 1991, shows a dropper with a truncated conical tip and an extending skirt of circular cross-section.

Some special problems are addressed in various patents. U.S. Pat. No. 5,154,702, issued to Mark L. Foyil on Oct. 13, 1992, discloses a dropper system that enables a user to select a variety of given dosages. The system also provides for securing and sealing means.

Improved means of securing and sealing are also seen in other patents, such as U.S. Pat. No. 2,854,003, issued to Nathan C. Kirsch on Sep. 30, 1958. A bottle closure is disclosed that involves a dropper-like device that has a bulb, a tube, a plug, and a cylindrical horizontal flange. The device is instrumental in the sealing of the bottle, which is accomplished by combining a screw cap with the dropper. Great Britain Patent No. 814,161, issued to Doria Nina Robineau on May 27, 1959, presents another instance wherein a bottle closure which is also a dropper is intended to provide a strong seal.

In U.S. Pat. No. 3,379,196, issued to Joseph M. Mitchell on Apr. 23, 1968, a dropper is described that is configured in three pieces, which are structured to fit together to provide a strong sealing connection. French Patent No. 934,688, issued to Francoise-Felix-Joseph Message on Jan. 19, 1948, concerns itself specifically with improvements in a stopper for a dropper.

French Patent No. 949,294, issued to Louis Menot on Feb. 14, 1948, is concerned with using methods, similar to those involved in droppers, to move small quantities of ink into the reservoir of a pen. In U.S. Pat. No. 2,005,091, issued to Walter E. Kuenstler on Jun. 18, 1935, a dropper mechanism is incorporated in a bottle cap and spreading device, for use particularly with condiments.

None of the above inventions and patents, taken either singly or in combination, is seen to describe the instant invention as claimed.

SUMMARY OF THE INVENTION

The present invention provides an improved device for applying liquid medicaments, particularly in enclosed areas such as under a toe or finger nail. The applicator of the present invention employs the concept of a dropper which terminates in a spatulate end portion, whose thinness and rounded edges allow it to slip under a nail so as to dispense medicine directly to the nail bed. The spatulate end portion has an inner shaft portion that may be strictly tubular, may be tapered, or may flared. The inner shaft portion is the end part of a thin tubular inner shaft which runs the length of the applicator to connect to a suction bulb, which is of course essential to the dropper function. The spatulate end portion is connected integrally by a transition portion to an outer cylindrical shaft, which encircles the inner shaft protectively. The top of the outer shaft broadens out into a screw cap portion that has inner threads. The screw cap in turn is united with a winged support member that helps steady and support the fingers of the user. The suction bulb and inner shaft are joined with the rest of the applicator by way of toroidal lips and friction. Alternatively, the inner shaft may be eliminated and the outer shaft instead used as the fluid tube for the dropper mechanism.

Accordingly, it is a principal object of the invention to provide a medicament applicator that terminates at one end to a a spatulate end portion capable of slipping under a nail.

It is a further object of the invention to provide a medicament applicator with a very thin, rounded-edge spatulate end portion that may be tapered.

It is an object of the invention to provide a medicament applicator with a spatulate end portion that has an inner shaft portion which may be cylindrical or tapered cylindrical, or may extend broadly through the end portion.

It is also an object of the invention to provide a medicament applicator having a thin tubular inner shaft that connects at the top to a suction bulb, runs the length of the fluid applicator, and terminates in a release opening at the bottom of a spatulate end portion.

It is another object of the invention to provide a medicament applicator having an outer cylindrical shaft protecting an inner shaft.

Still another object of the invention is to provide a medicament applicator including a screw cap with inner threads that is integral to an outer shaft.

It is another principal object of the invention to provide a winged member, integral with a screw cap, that aids in supporting an administering finger or fingers during application of fluid.

It is an alternative object of the invention to provide a medicament applicator having only one longitudinal shaft.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
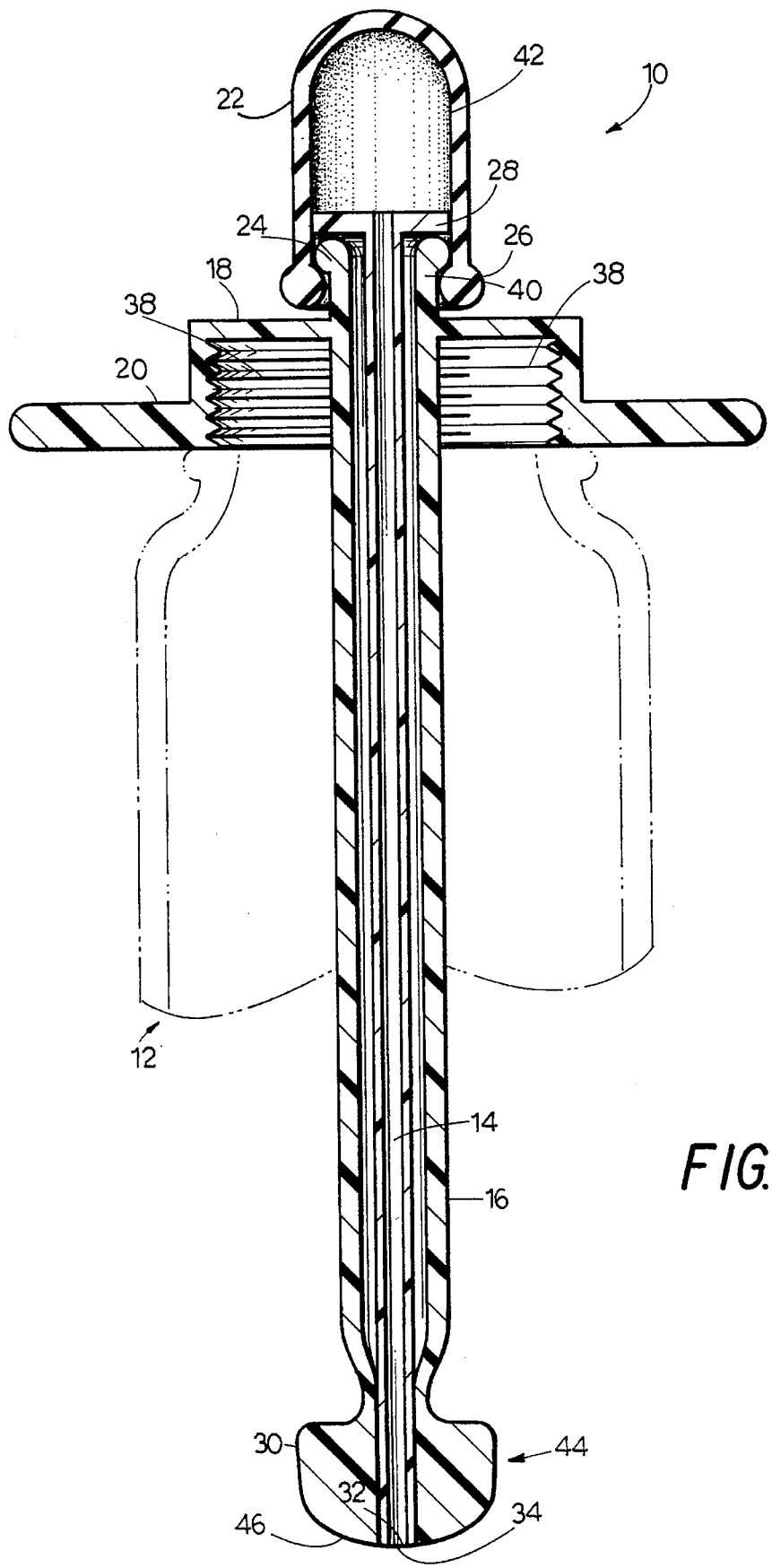
FIG. 1 is an cross-sectional view of an medicament applicator according to the present invention.

Referring now to FIG. 1, the present invention is an applicator, generally designated 10, which is particularly adapted for transmitting anti-fungal medicine to a toenail or fingernail bed. The applicator 10 is designed to cooperate with any typical bottle 12, having a threaded outer lip, such as would contain a relevant liquid medicine. The applicator 10 conveys the medicine to the nail bed directly, rather than using the common, less efficient method of brushing the medicine on the affected nail to soak through into the nail bed. The applicator 10, which, for the most part, is preferably made of plastic, also provides means to help the user most dexterously apply the medicine involved.

The applicator 10 generally includes an inner tubular shaft 14 encircled by an outer cylindrical shaft 16. Integral to the outer cylindrical shaft 16 at the top are a screw cap 18 and a winged member finger support 20. Also positioned at the top of the device is a suction bulb 22 and a pair of complementary toroidal lips 24 and 26 that help to join the suction bulb 22 to the outer cylindrical shaft 16. Securement is also facilitated by a flanged horizontal lip 28 at the top of the inner tubular shaft 14. Most important to the function of the applicator 10 is the spatulate portion 30 at the lower end of the outer cylindrical shaft 16. The spatulate portion 30 receives within it the inner tubular shaft 14, which terminates with an aperture 32 at a release opening 34 positioned at the extreme lower end of portion 30.

Near the top of the applicator 10, the inner tubular shaft 14 connects to the suction bulb 22 in order to provide a dropper mechanism. In typical dropper fashion, the inner tubular shaft 14 is evacuated by squeezing the suction bulb 22, which is preferably made of rubber or a flexible plastic. Medicine is then sucked up from the bottle 12 into the inner tubular shaft 14.

Figure 2:
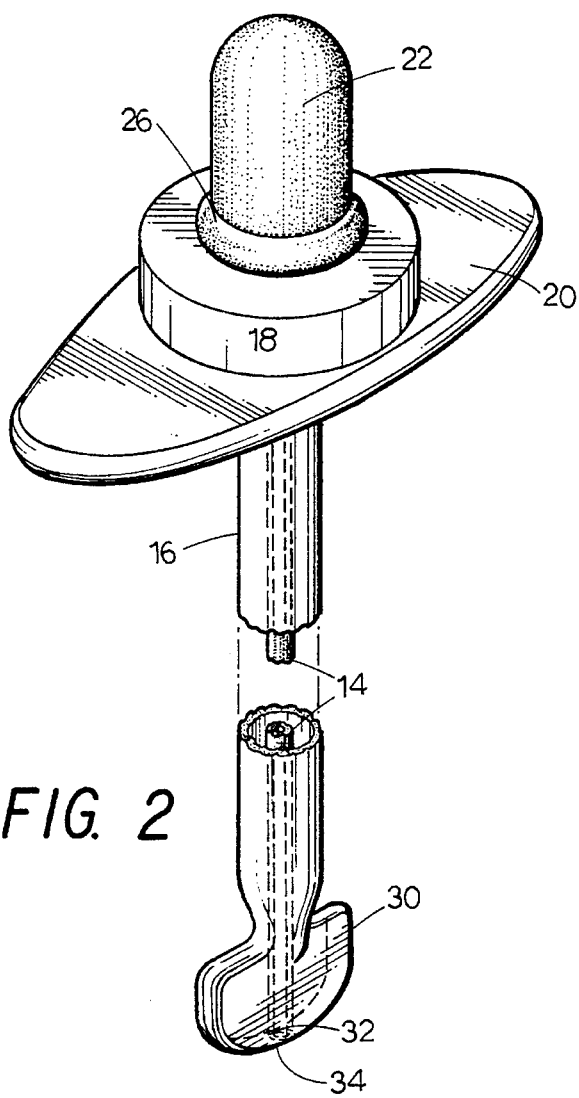
FIG. 2 is a perspective view of the present invention.
Figure 4:
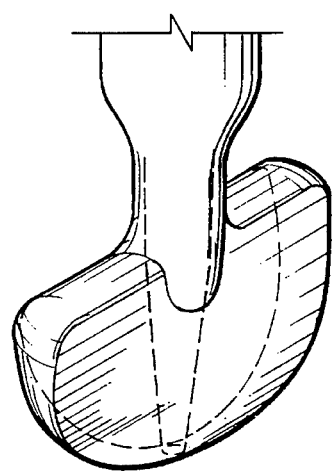
FIG. 4 is a perspective detail of another embodiment of the lower portion of the present invention.
Figure 5:
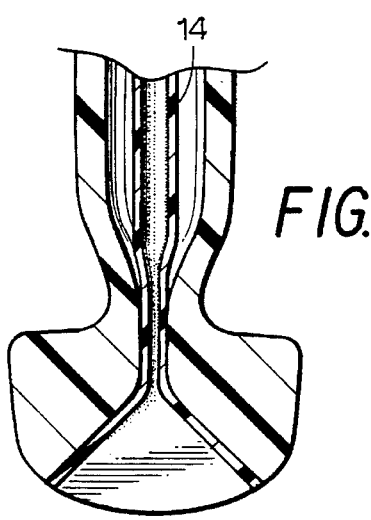
FIG. 5 is a cross-sectional detail of another embodiment of the lower portion of the present invention.
Figure 6:
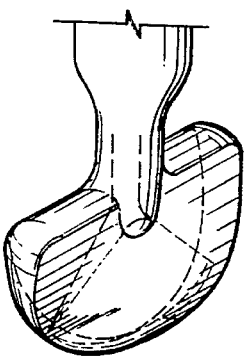
FIG. 6 is a perspective detail of another embodiment of the lower portion of the present invention.

The inner tubular shaft 14 is preferably made of plastic or glass. It may be of constant circular cross-section, as shown in FIGS. 1 and 2. Alternatively, the inner tubular shaft 14 may taper inward at its bottom, proximate to and/or within the spatulate portion 30. Another possibility, which may be combined with inward tapering, is for the inner tubular shaft 14 within the spatulate portion 30 to broaden to form a larger reservoir 36. Such alternatives are shown in FIG. 5, and are illustrated in FIGS. 4 and 6 by the configuration of the dotted line inner shapes, which may receive the bottom portion of an alternatively shaped inner tubular shaft 14.

In general the inner tubular shaft 14 is very thin. For its protection and for ease of use, the inner tubular shaft 14 is thus surrounded by an outer cylindrical shaft 16.

Handling of the applicator 10 is also facilitated at its top by various integral attachments to the outer cylindrical shaft 16. Referring again to FIGS. 1 and 2, a screw cap 18 with inner threads 38 is joined to the outer cylindrical shaft 16. Connected to the screw cap 18 is a winged member 20 that is oblong and is positioned perpendicularly to the outer cylindrical shaft 16. The user, when applying medicine retained within the applicator 10, is able to use the winged member 20 as a finger support in order to most carefully and efficiently transmit the medicine to needed sites. The winged member 20 may be curved, as shown, or may, for instance, be rectangular in horizontal cross-section.

Also integral to the outer cylindrical shaft 16 is the first toroidal lip 24, shown in both FIGS. 1 and 2. The first toroidal lip 24 sits atop a vertical projection 40 of the outer cylindrical shaft 16, and is complementary to the second toroidal lip 26, which rims the bottom of the suction bulb 22. The two toroidal lips 24 and 26 allow the suction bulb 22 to be secured onto the outer cylindrical shaft 16, and to stay secured while the fluid applicator 10 is being squeezed in use.

Proximate to the toroidal lips 24 and 26 is the horizontal flange 28, which is integral with the top of the inner tubular shaft 14. The horizontal flange 28 touches the inner surface 42 of the suction bulb 22, and rests on top of the first toroidal lip 24. This arrangement provides for a secure mechanism while the fluid applicator 10 is at rest or in use.

Referring now to all Figures, at the bottom of the applicator 10 and integral with the outer cylindrical shaft 16 is the applicator's most valuable aspect, the spatulate portion 30 and the features within it. The portion 30, which is very thin, resembles somewhat a spatula. In using the applicator 10, the spatulate portion 30 is inserted under a relevant nail and the suction bulb 22 is squeezed to release the necessary medicine. This insertion may be assisted, in some fungi sufferers, by the previous partial detachment of the nail from its bed. At any rate, the spatulate portion 30, by allowing the medicine to be directly transmitted to the unhealthy tissue, greatly increases the efficacy of treatment.

The spatulate portion 30 has rounded edges 44, so as not to unduly irritate sensitive tissue. The spatulate portion also has a broad bottom edge 46 to assist in the insertion process. The dispenser may be of uniform thickness, or may taper, becoming thinner toward the bottom 46.

At its bottom 46 the spatulate dispenser 30 has a release opening through which medicine enters and exits. The release opening 34 may be very small, as depicted in FIG. 4. Alternatively, if there is a broad reservoir 36 in the portion of the inner tubular shaft 14 within the spatulate portion 30, the release opening 34 is also broad. It may be somewhat oblong, as shown in FIG. 6. Obviously, whatever its shape, the release opening 34 is proximate to a complementary aperture 32 in the end of the inner tubular shaft 14.

Figure 3:
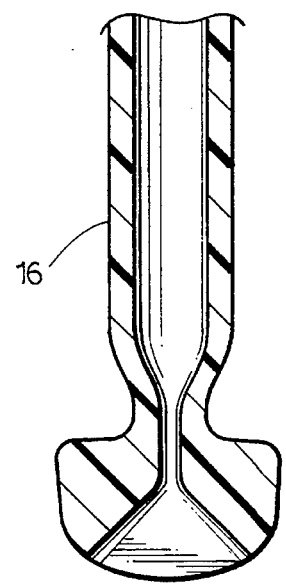
FIG. 3 is a cross-sectional detail of another embodiment of the lower portion of the present invention.

In an alternative embodiment, the inner tubular shaft 14 may be dispensed with and the outer cylindrical shaft 16, integral with the various parts as described above, may serve as the fluid-receiving tube. This arrangement, shown in cross-section in FIG. 3, may have any of the variety of configurations with the spatulate portion 30 that were described above with reference to the inner tubular shaft 14.

It is to be understood that the present invention is not limited to the embodiments described above, but encompasses any and all embodiments within the scope of the following claims.

I claim:

1. An applicator for use in administering medicine under nails, comprising:

a suction bulb, an inner tubular shaft having one end attached to said suction bulb and a second end terminating in a release opening, an outer cylindrical shaft encircling said tubular shaft, said outer cylindrical shaft having a spatulate end portion integral with said outer shaft said second end of said inner tubular shaft being coterminous with said spatulate end portion.

2. The applicator according to claim 1, wherein said spatulate end portion is very thin with rounded edges.

3. The applicator according to claim 1, wherein said spatulate end portion is tapered.

4. The applicator according to claim 1, wherein said inner tubular shaft includes a tapered portion within said spatulate end portion.

5. The applicator according to claim 1, wherein said inner tubular shaft includes a broadened portion within said spatulate end portion.

6. The applicator according to claim 1, wherein said release opening is circular.

7. The applicator according to claim 1, wherein said release opening is oblong.

8. The applicator according to claim 1, further including a screw cap, wherein said screw cap possesses internal threads and said screw cap is integral with a top portion of said outer cylindrical shaft.

9. The applicator according to claim 8, wherein said screw cap includes a winged member to provide finger support.

10. The applicator according to claim 9, wherein said winged member is oblong and is positioned perpendicularly to said outer cylindrical shaft.

11. The applicator according to claim 1, further including a first toroidal lip integral with the top of said outer cylindrical shaft.

12. The applicator according to claim 11, further including a second toroidal lip, said second toroidal lip being integral with said suction bulb and complementary with said first toroidal lip to secure said suction bulb to the tog of said outer cylindrical shaft.

13. The fluid applicator according to claim 12, further including a horizontal flange, said horizontal flange being integral with the top of said tubular shaft, said horizontal flange further resting on top of said first toroidal lip, and said horizontal flange further touching said inside surface of said suction bulb.

* * * * *